US00PP27123P2

(12) United States Plant Patent
van den Hoogen

(10) Patent No.: US PP27,123 P2
(45) Date of Patent: Aug. 30, 2016

(54) *HYPERICUM* PLANT NAMED 'ALLTANGO'

(50) Latin Name: *Hypericum hybrida*
Varietal Denomination: Alltango

(71) Applicant: Wilhelmus T. J. van den Hoogen, Cuijk (NL)

(72) Inventor: Wilhelmus T. J. van den Hoogen, Cuijk (NL)

(73) Assignee: Allplants Holding B.V., Cuijk (NL)

( * ) Notice: Subject to any disclaimer, the term of this patent is extended or adjusted under 35 U.S.C. 154(b) by 0 days.

(21) Appl. No.: 14/544,619

(22) Filed: Jan. 28, 2015

(51) Int. Cl.
*A01H 5/02* (2006.01)

(52) U.S. Cl.
USPC ..... Plt./442

(58) Field of Classification Search
USPC ..... Plt./442, 226
CPC ..... A01H 5/02; A01H 5/00
See application file for complete search history.

*Primary Examiner* — Kent L Bell
(74) *Attorney, Agent, or Firm* — C. A. Whealy

(57) ABSTRACT

A new and distinct cultivar of *Hypericum* plant named 'Alltango', characterized by its upright and outwardly spreading plant habit; moderately vigorous growth habit; dark green-colored leaves; freely flowering habit and high fruit density; and large glossy bright red-colored fruits.

1 Drawing Sheet

Botanical designation: *Hypericum hybrida.*
Cultivar denomination: 'ALLTANGO'.

BACKGROUND OF THE INVENTION

The present invention relates to a new and distinct cultivar of *Hypericum* plant, botanically known as *Hypericum hybrida*, typically grown as a cut-flower and hereinafter referred to by the name 'Alltango'.

The new *Hypericum* plant is a product of a planned breeding program conducted by the Inventor in Cuijk, The Netherlands. The objective of the breeding program is to create new *Hypericum* plants with strong stems and numerous attractive fruits.

The new *Hypericum* plant originated from an open-pollination in September, 2010 in Cuijk, The Netherlands of a proprietary selection of *Hypericum hybrida* identified as code number C10-33, not patented, as the female, or seed parent with an unknown selection of *Hypericum hybrida* as the male, or pollen, parent. The new *Hypericum* plant was discovered and selected by the Inventor as a single flowering plant from within the progeny of the stated open-pollination in a controlled greenhouse environment in Cuijk, The Netherlands in September, 2011.

Asexual reproduction of the new *Hypericum* plant by vegetative cuttings in a controlled greenhouse environment in Cuijk, The Netherlands since April, 2013 has shown that the unique features of this new *Hypericum* plant are stable and reproduced true to type in successive generations.

SUMMARY OF THE INVENTION

Plants of the new *Hypericum* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Alltango'.

These characteristics in combination distinguish 'Alltango' as a new and distinct *Hypericum* plant:

1. Upright and outwardly spreading plant habit.
2. Moderately vigorous growth habit.
3. Dark green-colored leaves.
4. Freely flowering habit and high fruit density.
5. Large glossy bright red-colored fruits.

Plants of the new *Hypericum* differ primarily from plants of the female parent selection in the following characteristics:

1. Plants of the new *Hypericum* produce larger fruits than plants of the female parent selection.
2. Plants of the new *Hypericum* and the female parent selection differ in fruit color as plants of the female parent selection have dark pinkish red-colored fruits.

Plants of the new *Hypericum* can be compared to plants of the *Hypericum hybrida* 'Allfiesta', not patented. In side-by-side comparisons, conducted in Cuijk, The Netherlands, plants of the new *Hypericum* differed primarily from plants of 'Allfiesta' in the following characteristics:

1. Plants of the new *Hypericum* had larger leaves than plants of 'Allfiesta'.
2. Plants of the new *Hypericum* had larger fruits than plants of 'Allfiesta'.

BRIEF DESCRIPTION OF THE PHOTOGRAPH

The accompanying colored photograph illustrates the overall appearance of the new *Hypericum* plant showing the colors as true as it is reasonably possible to obtain in colored reproductions of this type. Colors in the photograph may differ slightly from the color values cited in the detailed botanical description which accurately describe the actual colors of the new *Hypericum* plant.

The photograph comprises a side perspective view of a typical fruiting stem of 'Alltango'.

DETAILED BOTANICAL DESCRIPTION

Plants used for the aforementioned photographs and following description were grown in September in an outdoor nursery in Cuijk, The Netherlands and under cultural practices typical of commercial cut-flower *Hypericum* production. During the production of the plants, day temperatures ranged from 13° C. to 26° C. and night temperatures ranged from 6° C. to 16° C. Plants were one year old when the photograph and description were taken. In the following description, color references are made to The Royal Horticultural Society Colour Chart, 2007 Edition, except where general terms of ordinary dictionary significance are used.

Botanical classification: *Hypericum hybrida* 'Alltango'.

Parentage:

*Female, or seed, parent*.—Proprietary selection of *Hypericum hybrida* identified as code number C10-33, not patented.

*Male, or pollen, parent*.—Unknown selection of *Hypericum hybrida*, not patented.

Propagation:

*Type cutting*.—Vegetative cuttings.

*Time to initiate roots, summer*.—About 10 to 14 days at temperatures about 12° C. to 30° C.

*Time to initiate roots, winter*.—About 14 to 20 days at temperatures about 12° C. to 22° C.

*Time to produce a rooted young plant, summer*.—About 24 to 32 days at temperatures ranging from 12° C. to 30° C.

*Time to produce a rooted young plant, winter*.—About 28 to 36 days at temperatures ranging from 12° C. to 22° C.

*Root description*.—Fine, fleshy; white in color.

*Rooting habit*.—Freely branching; dense.

Plant description:

*Plant and growth habit*.—Perennial shrub; upright and outwardly spreading plant habit, narrow inverted triangle; moderately vigorous to vigorous growth habit.

*Branching habit*.—Moderately freely basal branching habit; pinching enhances lateral branch development.

*Plant height*.—About 58.4 cm.

*Plant width* (*spread*).—About 21.4 cm.

*Lateral branch description*.—Length: About 31.3 cm. Diameter: About 4 mm. Internode length: About 6 cm. Strength: Moderately strong to strong. Texture: Smooth, glabrous. Luster: Moderately glossy. Color, developing: Close to 181A to 181B; youngest stems tinged with close to 145A to 145B. Color, fully developed: Close to N199C to N199D.

Leaf description:

*Arrangement*.—Opposite, simple; sessile.

*Length*.—About 7.1 cm.

*Width*.—About 4 cm.

*Shape*.—Ovate.

*Apex*.—Broadly acute.

*Base*.—Cordate to reniform.

*Margin*.—Entire.

*Texture, upper and lower surfaces*.—Smooth to slightly rugose; glabrous.

*Luster, upper and lower surfaces*.—Slightly glossy.

*Venation pattern*.—Pinnate.

*Color*.—Developing leaves, upper surface: Close to between 152A and 199A. Developing leaves, lower surface: Close to 176B. Fully expanded leaves, upper surface: Close to N137B; venation, close to 147D. Fully expanded leaves, lower surface: Close to 148B; venation, close to 144A.

Flower description:

*Flower type, arrangement and flowering habit*.—Single rotate flowers arranged in terminal and axillary compound cymes; freely flowering habit with about six flowers per cyme; flowers face mostly upright.

*Fragrance*.—None detected.

*Natural flowering season*.—Plants flower continuously from mid-June to mid-August in The Netherlands; plants begin flowering about ten months after planting.

*Flower longevity*.—Flowers last about two or three days on the plant; flowers not persistent.

*Fruit longevity*.—About one month on the plant.

*Flower buds*.—Length: About 7 mm. Diameter: About 7 mm. Shape: Globular. Color: Close to 151D; towards the apex, close to 21A.

*Inflorescence height*.—About 6.7 cm.

*Inflorescence diameter*.—About 7.7 cm.

*Flower diameter*.—About 3 cm.

*Flower depth* (*height*).—About 2.2 cm.

*Petals*.—Quantity and arrangement: Five in a single whorl. Length: About 1.4 cm. Width: About 1 cm. Shape: Ovate; concave; very slightly reflexed. Apex: Bluntly acute. Base: Attenuate. Margin: Entire. Texture, upper and lower surfaces: Smooth, glabrous. Luster, upper surface: Matte. Luster, lower surface: Slightly glossy. Color: When opening and fully opened, upper surface: Close to 12A; color becoming closer to 14B with development. When opening and fully opened, lower surface: Close to 13B.

*Sepals*.—Quantity and arrangement: Five in a single whorl. Length: About 1.1 cm. Width: About 8 mm. Shape: Broadly ovate to orbicular. Apex: Broadly acute to obtuse. Base: Broadly cuneate. Margin: Entire. Texture, upper and lower surfaces: Smooth, glabrous. Luster, upper and lower surfaces: Dull, matte. Color: When opening, upper surface: Close to 141A. When opening, lower surface: Close to 143C; towards the apex, tinged with close to 187B. Fully opened, upper surface: Close to 141A. Fully opened, lower surface: Close to 137C; towards the apex, slightly tinged with close to 187B.

*Peduncles*.—Length: About 2.5 cm. Diameter: About 3 mm. Texture: Smooth, glabrous. Strength: Moderately strong. Aspect: Erect to about 50° from vertical. Color: Close to 175A.

*Pedicels*.—Length: About 3.3 cm. Diameter: About 2 mm. Texture: Smooth, glabrous. Strength: Moderately strong. Aspect: Erect to about 50° from vertical. Color: Close to 144B to 144C strongly tinged with close to 175A.

*Reproductive organs*.—Stamens: Quantity per flower: About 80. Filament length: About 1.5 mm. Filament color: Close to 12A. Anther length: About 0.5 mm. Anther shape: Broadly oval. Anther color: Close to 22A. Pollen amount: Scarce. Pollen color: Close to 11A. Pistils: Quantity per flower: Single pistil with three stigmas. Pistil length: About 4 mm. Stigma shape: Club-shaped. Stigma color: Close to 35A. Style length: About 3.5 mm. Style color: Close to 150C. Ovary color: Close to 150D.

*Fruits*.—Length: About 1.3 cm. Diameter: About 1.3 cm. Shape: Spherical. Texture: Smooth, glabrous. Luster: Glossy. Color: Close to 46B.

*Seeds*.—Length: About 0.9 mm. Diameter: About 0.5 mm. Color: Close to 200A.

Disease & pest resistance: Plants of the new *Hypericum* have not been observed to be resistant to pathogens and pests common to *Hypericum* plants.

Temperature tolerance: Plants of the new *Hypericum* have been observed to tolerate high temperatures about 30° C. and to be hardy to USDA Hardiness Zone 7.

It is claimed:

1. A new and distinct *Hypericum* plant named 'Alltango' as illustrated and described.

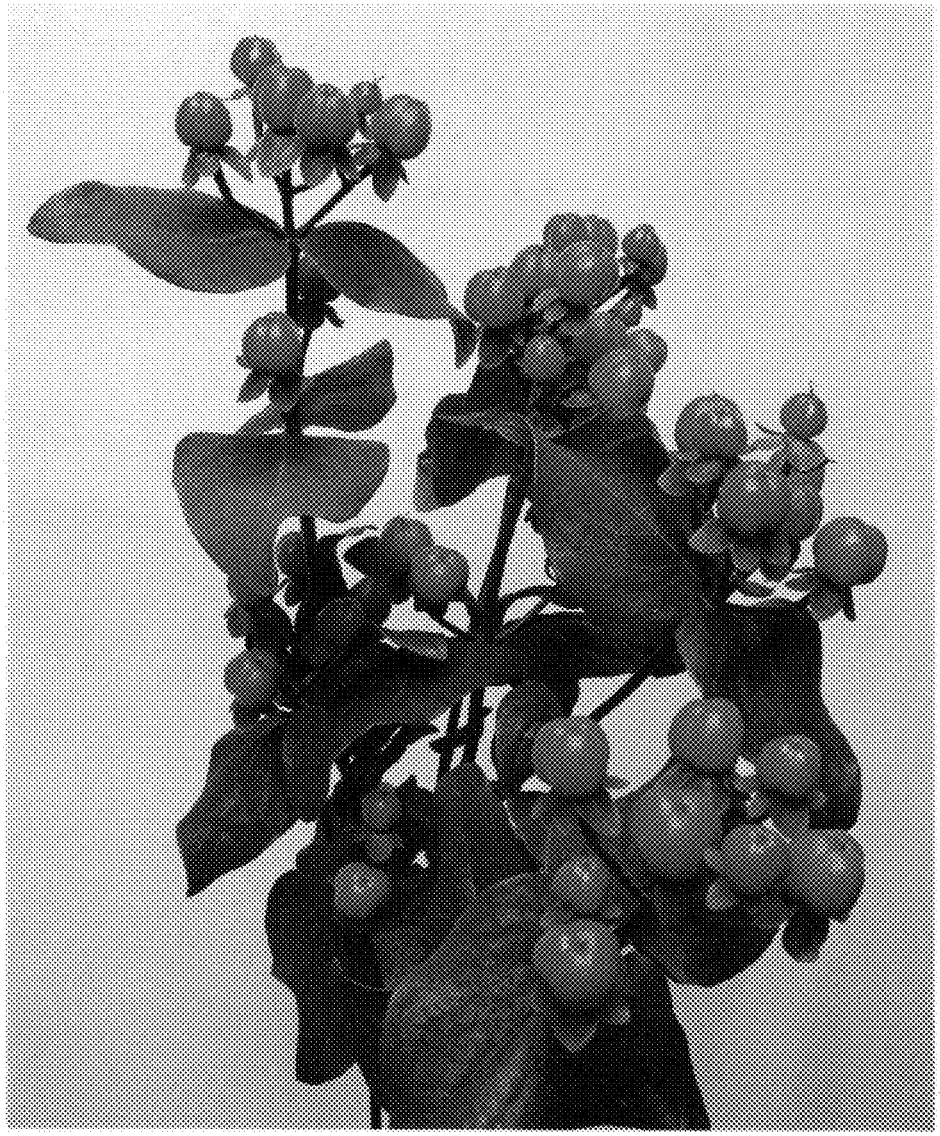

* * * * *